(12) United States Patent
Floyd et al.

(10) Patent No.: US 7,588,541 B2
(45) Date of Patent: Sep. 15, 2009

(54) METHOD AND SYSTEM FOR POSITIONING A MEDICAL DEVICE AT ONE OR MORE ANGLES RELATIVE TO AN IMAGING PROBE

(75) Inventors: Jared Floyd, Lynnwood, WA (US); Steven Bunce, Sedro Woolley, WA (US)

(73) Assignee: SonoSite, Inc., Bothell, WA (US)

( * ) Notice: Subject to any disclaimer, the term of this patent is extended or adjusted under 35 U.S.C. 154(b) by 873 days.

(21) Appl. No.: 10/766,707

(22) Filed: Jan. 28, 2004

(65) Prior Publication Data

US 2005/0131291 A1 Jun. 16, 2005

Related U.S. Application Data

(60) Provisional application No. 60/528,505, filed on Dec. 10, 2003.

(51) Int. Cl.
*A61B 8/00* (2006.01)
(52) U.S. Cl. .................................................. 600/461
(58) Field of Classification Search ................. 600/309, 600/411, 415, 417, 427, 461, 466, 443, 471; 606/14, 46, 108
See application file for complete search history.

(56) References Cited

U.S. PATENT DOCUMENTS

| | | | | | |
|---|---|---|---|---|---|
| 4,346,717 | A | * | 8/1982 | Haerten ....................... | 600/461 |
| 4,469,106 | A | * | 9/1984 | Harui .......................... | 600/461 |
| 4,576,175 | A | * | 3/1986 | Epstein ....................... | 600/461 |
| 4,763,662 | A | * | 8/1988 | Yokoi .......................... | 600/461 |
| 4,899,756 | A | * | 2/1990 | Sonek ......................... | 600/461 |
| 5,052,396 | A | | 10/1991 | Wedel et al. | |
| 5,076,279 | A | * | 12/1991 | Arenson et al. ............. | 600/461 |
| 5,758,650 | A | * | 6/1998 | Miller et al. ................. | 600/461 |
| 5,924,992 | A | * | 7/1999 | Park et al. ................... | 600/461 |
| 5,941,889 | A | * | 8/1999 | Cermak ....................... | 606/130 |
| 5,967,985 | A | * | 10/1999 | Hayakawa ................... | 600/440 |
| 6,095,981 | A | | 8/2000 | McGahan | |
| 6,296,614 | B1 | | 10/2001 | Pruter | |

(Continued)

FOREIGN PATENT DOCUMENTS

EP 0 467 291 A1 7/1990

(Continued)

OTHER PUBLICATIONS

Partial European Search Report issued for EP 04 25 7622, dated May 25, 2005.

*Primary Examiner*—Brian Casler
*Assistant Examiner*—Parikha S Mehta
(74) *Attorney, Agent, or Firm*—Fulbright & Jaworski L.L.P.

(57) ABSTRACT

In one embodiment, a needle guide is attached to the end of an ultrasonic probe in a manner such that the needle will follow a known trajectory under control of the needle guide. The surgeon then positions the needle guide by looking at the ultrasound image formed from the ultrasound radiated from the probe. In one embodiment, the needle guide has a release mechanism that allows the needle (or other medical device) that had been positioned in the guide to remain in the patient when the probe is removed. In one embodiment, the needle guide is designed to be releasably mounted to a bracket which, in turn, is releasably mounted to the end of the probe.

18 Claims, 7 Drawing Sheets

U.S. PATENT DOCUMENTS

| | | | |
|---|---|---|---|
| 6,361,499 B1 * | 3/2002 | Bates et al. | 600/461 |
| 6,475,152 B1 * | 11/2002 | Kelly et al. | 600/461 |
| 6,612,990 B1 | 9/2003 | Pruter | |
| 6,616,610 B2 | 9/2003 | Steininger et al. | |
| 6,758,817 B1 * | 7/2004 | Pruter et al. | 600/461 |
| 6,814,704 B2 * | 11/2004 | Weilandt | 600/461 |
| 7,087,024 B1 * | 8/2006 | Pruter | 600/461 |
| 2004/0133111 A1 * | 7/2004 | Szczech et al. | 600/461 |

FOREIGN PATENT DOCUMENTS

JP     11 12 8237     5/1999

* cited by examiner

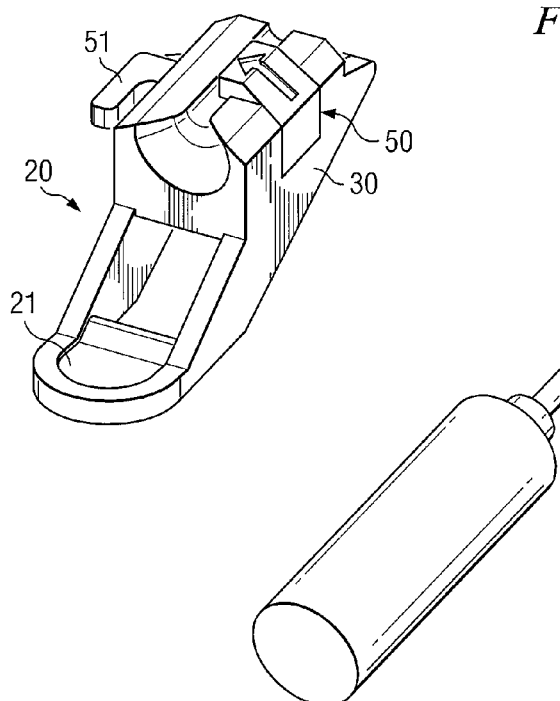
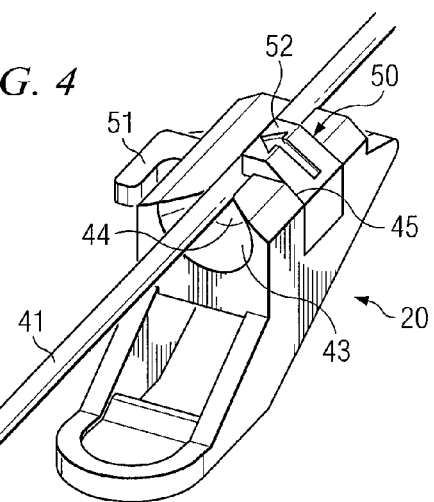
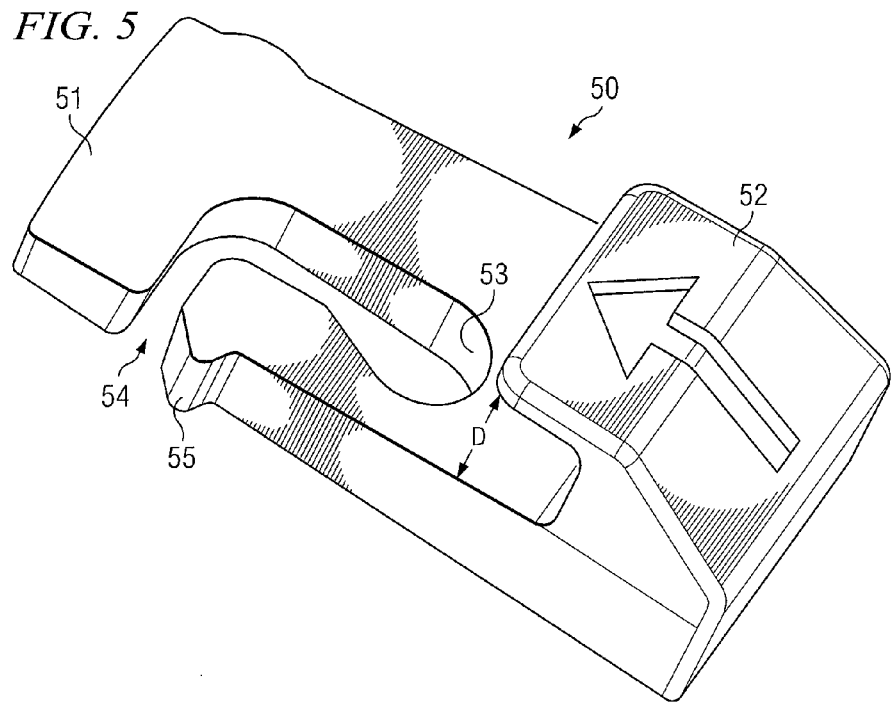

*FIG. 9A*
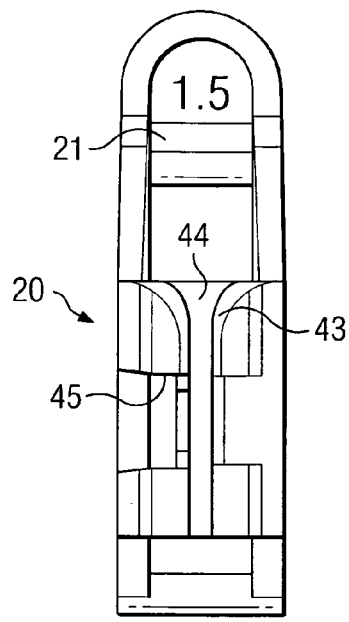
*FIG. 9C*
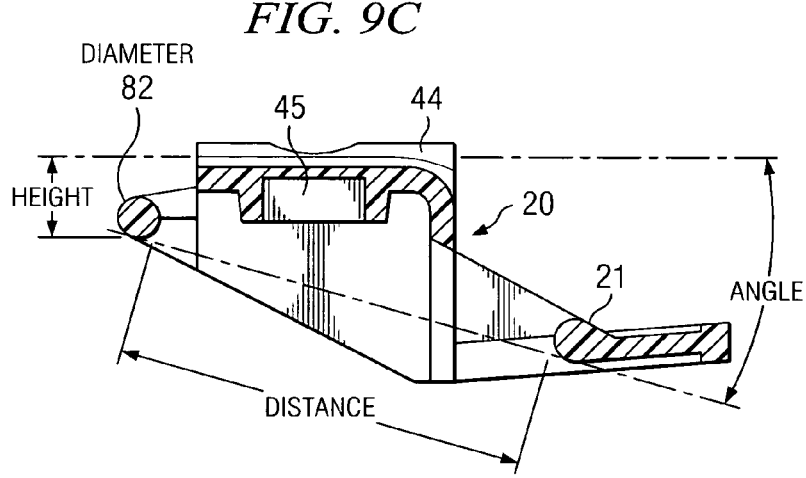
*FIG. 9B*
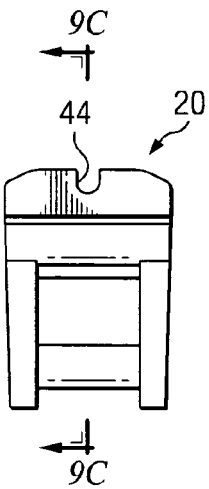
*FIG. 9D*
| DIMENSION TABLE | | | | |
|---|---|---|---|---|
| DEPTH | 1.5 cm | 2.5 cm | 3.5 cm | 4.5 cm |
| ANGLE | 28.1° ± .4° | 15.7° ± .4° | 10.5° ± .4° | 6.4° ± .4° |
| HEIGHT | .190 in | .190 in | .235 in | .254 in |
| DIAMETER (2X) | .094 in | .094 in | .094 in | .094 in |
| DISTANCE | .982 in | .982 in | .982 in | .982 in |

METHOD AND SYSTEM FOR POSITIONING A MEDICAL DEVICE AT ONE OR MORE ANGLES RELATIVE TO AN IMAGING PROBE

CROSS-REFERENCE TO RELATED APPLICATION

This application claims priority to U.S. Provisional Patent Application No. 60/528,505 filed Dec. 10, 2003, entitled DEVICE FOR ASSISTING THE POSITIONING OF MEDICAL DEVICES, the disclosure of which is hereby incorporated by reference in its entirety.

TECHNICAL FIELD

This invention relates to medical positioning devices and more particularly to systems and methods for using imaging equipment, such as ultrasound, for assisting in the placement of a medical device.

BACKGROUND

Proper positioning of medical devices, such as needles, catheters, drills, saws and even scalpels, is critical in the proper performance of certain medical procedures. Often the surgeon must look at a screen while trying to manually position a medical device, and thus can not look directly at the device. This is difficult at best and sometimes results in improper angles of attack and could result in improper placement of the medical device.

SUMMARY

In one embodiment, a needle guide is attached to the end of an ultrasonic probe in a manner such that the needle will follow a known trajectory under control of the needle guide. The surgeon then positions the needle guide by looking at the ultrasound image formed from the ultrasound radiated from the probe.

In one embodiment, the needle guide has a release mechanism that allows the needle (or other medical device) that had been positioned in the guide to remain in the patient when the probe is removed.

In one embodiment, the needle guide is designed to be releasably mounted to a bracket which, in turn, is releasably mounted to the end of the probe.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DESCRIPTION OF THE DRAWINGS

FIG. 3 shows one embodiment of a medical device guide and release mechanism based on the embodiment of FIG. 1;
FIG. 4 shows one embodiment of a needle held by the medical device guide;
FIG. 5 shows details of one embodiment of the release mechanism based on the embodiment of FIG. 1;
FIGS. 9A, 9B, 9C and 9D show dimensional relationships of embodiments of the illustrated device guide.

DETAILED DESCRIPTION

Figure 1:
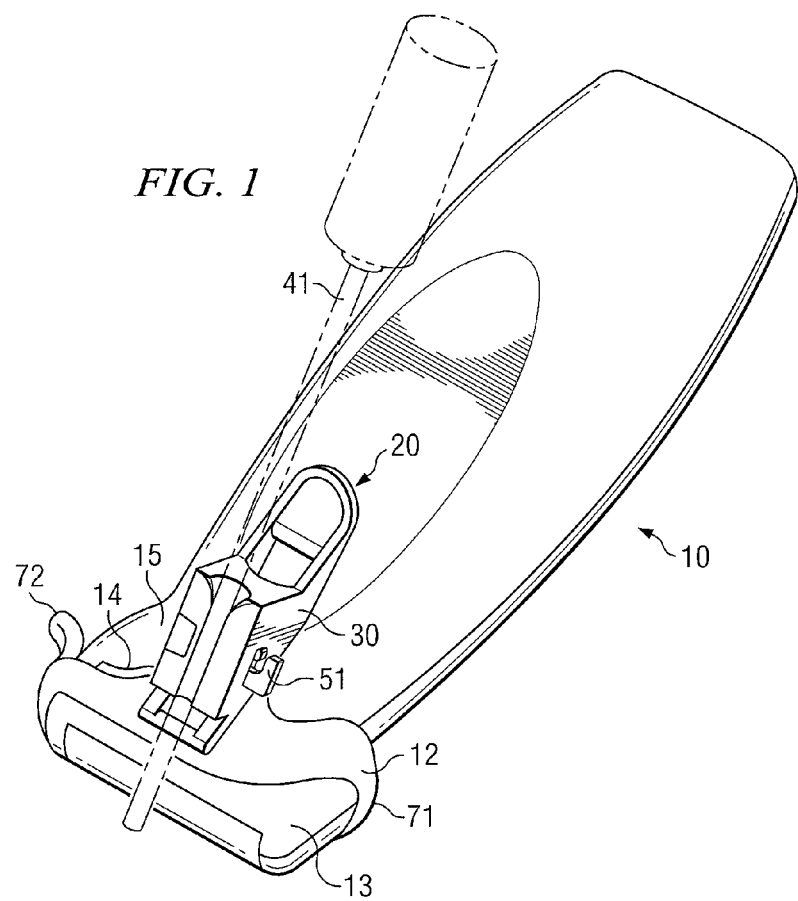
FIG. 1 shows one embodiment of a probe having a medical device positioning guide mounted thereon.
Figure 7A:
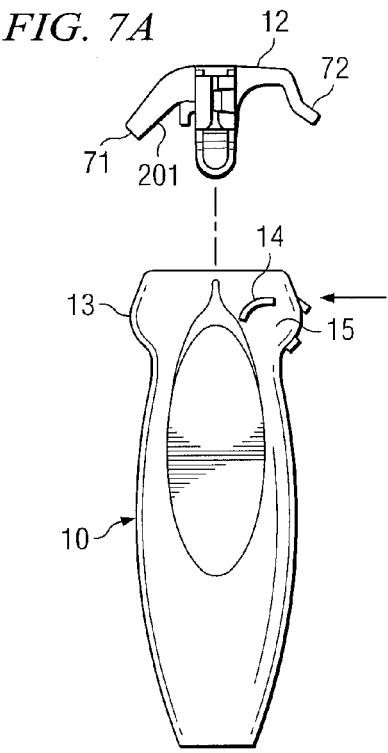
FIGS. 7A, 7B and 7C illustrate the releaseable mating of the device bracket with the probe.
Figure 7B:
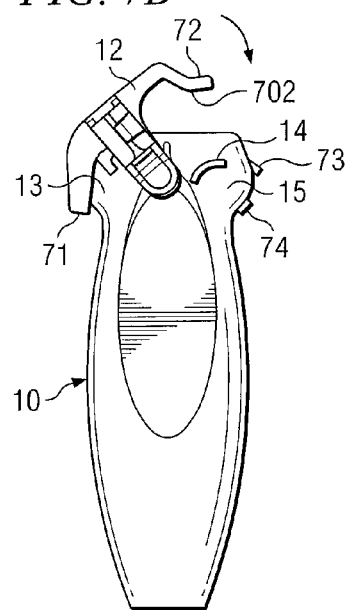
Figure 7C:
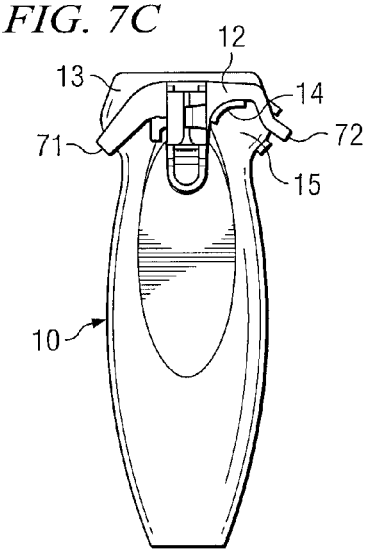

FIG. 1 shows one embodiment of probe 10 having bracket 12 releasably attached thereto. This attachment, for example, is by fitting a first side 71 of the bracket over protrusion 13 on probe 10, as shown in FIG. 7A. The other side 72 of the bracket fits over the other side 15 of probe 10 as shown in FIG. 7B, and locks between protrusions 73 and 74 up against slot 14 of probe 10 again, as shown in FIG. 7C. Slot 702 snaps over protrusion 73 to hold bracket 12 from swinging open. Probe 10, in the embodiment of FIG. 1, can be an ultrasound probe.

In operation, probe 10 (FIG. 1) sends ultrasound signals into the body and these signals then provide images of organs, fluids, etc which are otherwise hidden from view. When the probe is positioned properly, as determined by the images sent back by the ultrasound, the surgeon can then insert a needle, such as needle 41, (or other surgical instrument), knowing the instrument's trajectory based upon the received images. The trajectory is a preset by the selection of the device guide. The device guide establishes an angle of attack with respect to the proximal end of the probe. By extension, this angle of attack extends below the skin of the patient. In some cases, the image may contain a projection of the needle trajectory as an aide to the surgeon.

When the needle, or other device to be inserted, is positioned properly, the needle is slid forward so that its proximal end moves toward the patient and enters the patient. When the desired depth is reached, mechanism 50 is operated to release the needle thereby allowing probe 10, bracket 12 and needle guide 20 to be removed, leaving the needle (or other device) within the patient's body.

Figure 2:
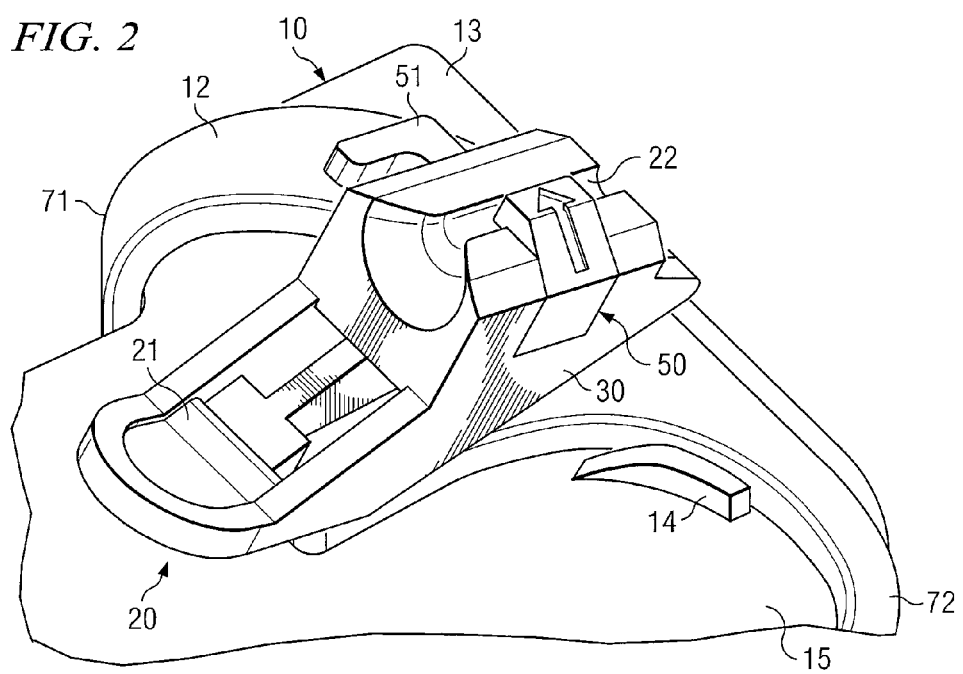
FIG. 2 shows a view of the positioning guide of FIG. 1.
Figure 8A:
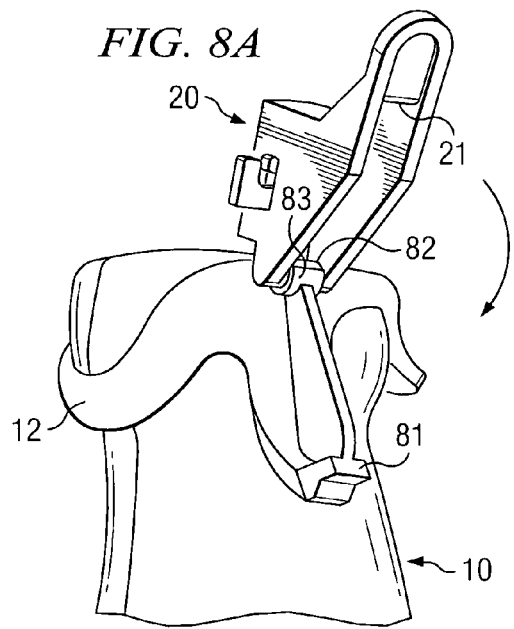
FIG. 8A, 8B and 8C illustrate the releaseable mating of the device guide with the device bracket.
Figure 8C:
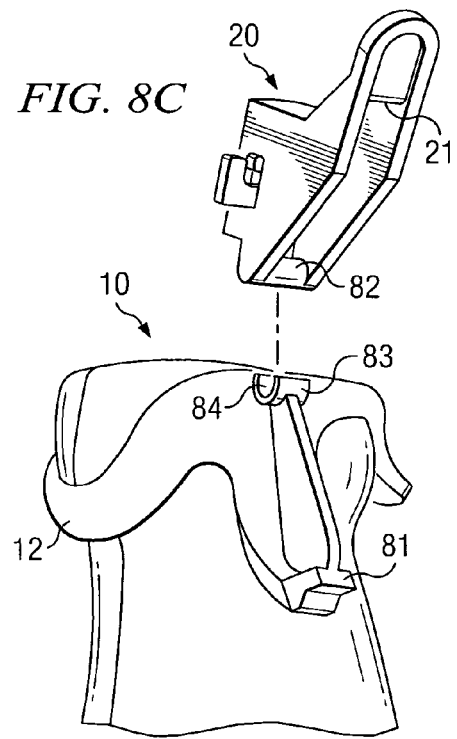
Figure 8B:
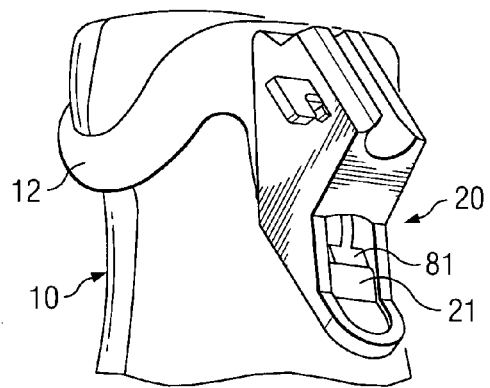

FIG. 2 shows bracket 12 having medical device guide 20 mounted thereon. Note that device 20 and device 12 can be a single structure if desired. Device 20 in the embodiment shown, is a device for holding a needle (shown in FIG. 4) within groove 22. Release control portion 50 holds the needle in position, while end portion 51 serves to release the needle when the needle has been properly positioned. If device 20 and device 12 are separate structures, they can be releasably mated as shown in FIGS. 8A and 8B. As shown in FIG. 8A, one end of device 20 is mated via pins 82 (shown in FIG. 8C) being inserted into bracket 83. Once pin 82 is positioned in bracket 83, guide 20 is rotated toward probe 10 and snaps in position under control of tab 81 of bracket 12 releaseably locking on edge 21 of device 20.

As shown in FIG. 3, device guide 30 consists of two parts: namely, guide 20 and release mechanism 50. Guide 30 snaps into bracket 12, as discussed above, attached to an ultrasound transducer. The device guide is manufactured to control the placement of devices, such as catheter and needles, to multiple depths, by changing the angle of attack at which the needle (or catheter) is presented to the transducer. The device guide is also manufactured to handle multiple gauges to accommodate specific diameter medical devices.

As shown in FIG. 4, guide 20 has lead-in 43 to make insertion of the needle (such as needle 41) into the guide easier. Needle 41 then rests in channel 44 along the longitudinal axis of probe 10 so that the needle is positioned in a specific trajectory with respect to the surface to be probed. In effect, the medical device (which typically would be an elongated device (needle) with a substantially round cross-section forms a closing angle with the proximal end of the guide (and the probe) so that when the probe is properly placed, the proximal end, when moved down the channel, will be positioned a given distance below the skin of the patient. This trajectory intersects the patient at the target depth (such as 1.5 cm.) as indicated on the needle guide. Various angles and respective depths for 1.5, 2.5, 3.5 and 4.5 cms are shown in FIG. 9A-9D.

FIG. 4 shows mechanism 50 (discussed in more detail with respect to FIGS. 6 and 7) mounted in slot 45 of guide 20. Release portion 52 is positioned over needle 41 and exerts pressure on needle 41 within groove 44. The pressure from portion 52 on the needle guide keeps the needle in proper orientation, but allows the user to slide the clamped needle toward the patient. The needle can then be positioned below the skin of the patient at the desired depth.

FIG. 5 shows mechanism 50 having flexible tab 55 to maintain a closed position and to prevent accidental opening. The geometry of mechanism 50, including dimension D, provides a specific amount of needle drag friction between the inserted needle and groove 44. Once the needle has been oriented into the desired position, tab 55 is flexed inward allowing mechanism 50 (and particularly overhang 52) to move away from groove 44, thereby allowing needle 41 to release from the device guide. This, then, allows needle 41 to remain in the patient when the probe is removed.

Figure 6:
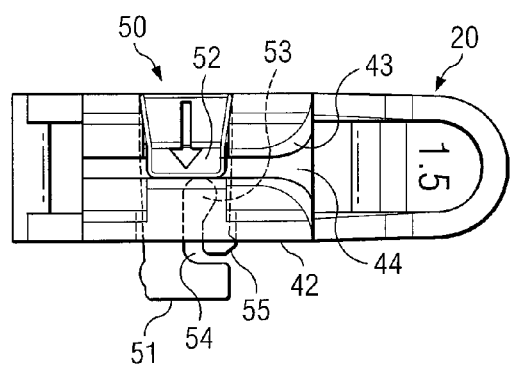
FIG. 6 illustrates how the release mechanism of FIG. 5 releasably mates with the device guide of FIG. 1.

FIG. 6 shows a top schematic view of mechanism 50 inserted in guide 20 with tab 55 locking against edge 42 of guide 20 prior to release of mechanism 50 from guide 20. Tab 55 flexes into slot 53 formed by opening 54.

FIGS. 9A-9D show dimensional relationships of embodiments of a device guide. FIG. 9A shows a top view of guide 20. FIG. 9B is an end view of guide 20 and FIG. 9C is a section 9C-9C taken through device 20 in FIG. 9B. FIG. 9D shows typical illustrative dimensions (keyed to FIG. 9C) for different depth guides.

Figure 10A:
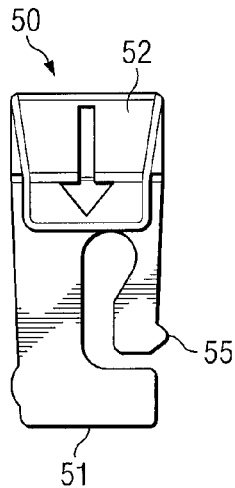
FIGS. 10A, 10B and 10C show dimensional relationships of embodiment of the illustrated release mechanism.
Figure 10B:
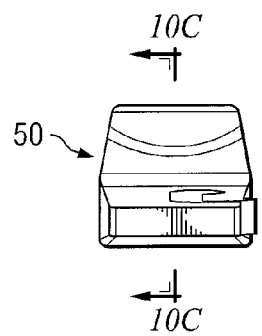
Figure 10C:
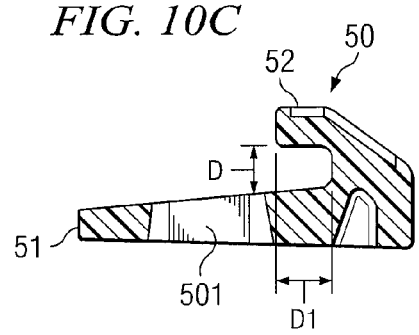

FIG. 10A shows a top view of mechanism 50. FIG. 10B shows the end view of mechanism 50 and FIG. 10C is a section 10C-10C taken through mechanism 50 in FIG. 10B. Dimension D is keyed to the diameter of the device to be held within the guide. For 18 gauge needles, this dimension would be 0.070 in for the embodiment shown, and dimension D1 would be 0.096 in. A typical length for mechanism 50 would be 0.564 in. If desired, portion 501 (FIG. 10C) can be tapered to better wedge needle 41 when in seating portion 44 of the guide.

Figure 11:
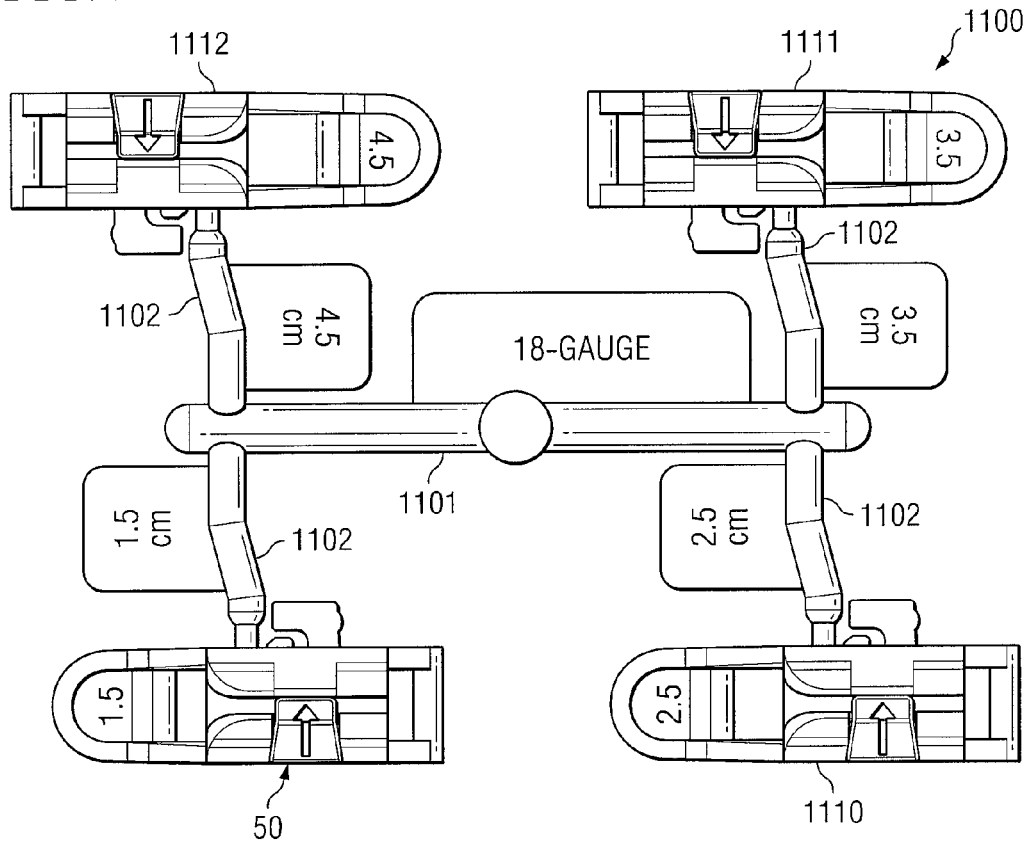
FIG. 11 shows one embodiment of packaging a plurality of device guides.

FIG. 11 shows one embodiment 1100 of the packaging for a plurality of needle guides, 50, 1110, 1111 and 1112. Each of the needle guides can have different target depths, or they can all have the same depth. Center holder 1101 has limbs 1102 for holding each guide. Any number of limbs can be used.

Figure 12:
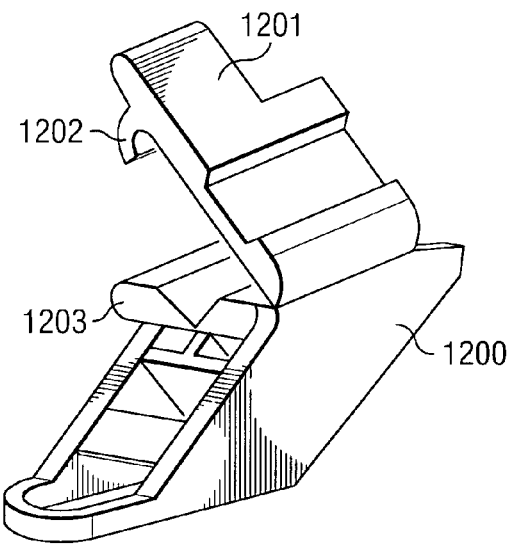
FIGS. 12 and 13 show alternate embodiments of the medical device guides.

FIG. 12 shows one alternate device guide 1200 with latch 1201 in the open position. As shown, latch 1202 will engage protrusion 1203 for latching purposes.

Figure 13:
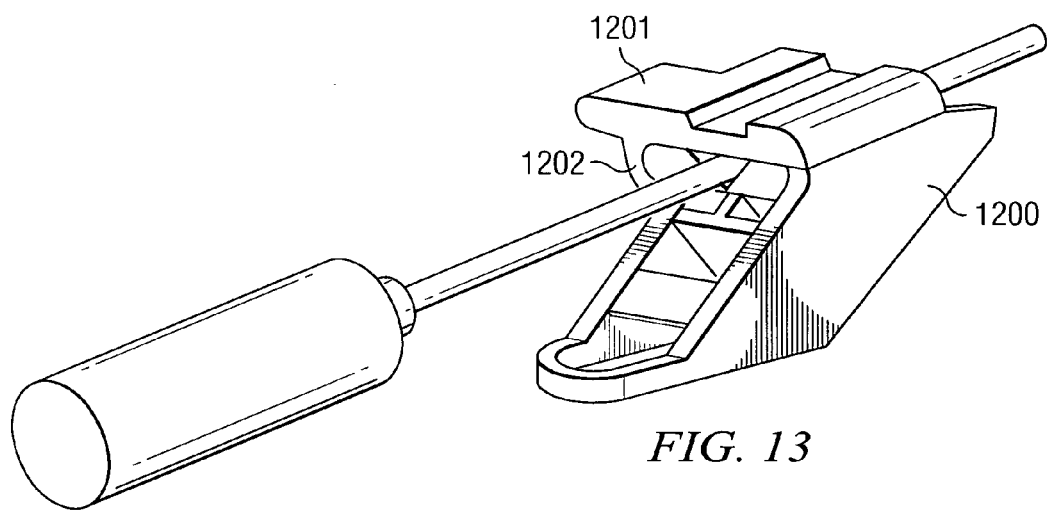

FIG. 13 shows guide 1200 in the latched position clamping needle 41 in position.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A guide for fastening to an ultrasonic probe, said probe operative for transmitting signals from said probe's proximal end through a patient's body for the purpose of creating an image; said guide comprising:
    at least one support configured to releasably attach to a proximal end of said probe, said support having a longitudinal seating area for positioning a rod therein;
    a latch configured to temporarily hold said rod in fixed position with respect to said patient so that a proximal end of said rod will follow a known trajectory with respect to a generated image of said patient's body; said latch configured to be fitted over said rod where said rod is seated in said seating area, said latch comprising a tapered wedge portion configured to be positioned below a seated rod; and
    a tab on said latch operable for allowing said latch to release said rod.

2. The guide of claim 1 wherein said latch is positioned perpendicular to said seating area and wherein said latch slides across said seating area.

3. The guide of claim 1 wherein said support comprises:
    a bracket for mating to said probe at said proximal end of said probe, and
    at least one pivot point for allowing said guide to release from said bracket.

4. The guide of claim 1 wherein said latch comprises:
    an overhang portion for positioning above said rod when said rod is in said seating area, said overhang portion preventing said rod from becoming disengaged from said guide without first moving said latch to its open position.

5. The guide of claim 1 wherein said latch comprises:
    a flexible tab for preventing said latch from moving from its closed to its open position.

6. The guide of claim 5 wherein said moving is perpendicular to said seated rod.

7. A method of releasably attaching a medical device to a probe, said method comprising:

positioning said medical device along a longitudinal axis of said probe;

clamping said medical device with respect to said probe so that an angle of attack of said clamped medical device remains constant with respect to a proximal end of said probe, said clamping controlled at least in part by a slidably coupled latch having a dimension keyed to a diameter of said medical device, wherein said slidably coupled latch comprises an upper surface and a lower surface, said lower surface including a wedge portion which tapers upward to define said dimension;

generating at least one image of structures below the surface of an object over which said proximal end of said probe moves, said image generation resulting at least in part from signals emitted from said proximate end of said probe;

sliding a proximal end of said clamped medical device toward said surface of said object along a trajectory predictable as a result of said generated image;

continuing to slide said proximal end of said clamped medical device along said trajectory to a position below said surface of said object; and releasing said clamped positioned medical device from said probe while said proximal end of said medical device remains positioned below said surface of said object.

8. The method of claim 7 wherein said positioning comprises:

inserting said medical device into a guide attached to said proximal end of said probe.

9. The method of claim 8 wherein said guide is configured to define a closing angle with respect to said proximal end of said probe and wherein said trajectory is predictable at least in part by said closing angle.

10. The method of claim 9 wherein said closing angle corresponds to a target depth of said positioned medical device below said surface of said object.

11. The method of claim 8 wherein said guide is releasably connected to said probe.

12. The method of claim 7 wherein said latch is positioned transverse to said longitudinal axis.

13. The method of claim 12 wherein at least a portion of said latch contains a ramp.

14. The method of claim 7 wherein said medical device has a round cross-section.

15. A method for releasably attaching a needle to a proximal end of an image generating probe, said method comprising:

positioning a guide support bracket at said proximal end of said probe, said guide support bracket configured to accept, one at a time, a plurality of needle guides each having either a different angle of attack or accepting a different gauge needle;

selecting a needle guide having a particular angle of attack with respect to said proximal end of said probe, said selected needle guide accepting a particular gauge;

releasably attaching said selected needle guide to said attached bracket; and releasably attaching a needle to said attached needle guide by sliding a clamping mechanism within said selected one of said needle guides so that the longitudinal axis of said needle lies along a longitudinal axis of said selected one of said needle guides, said needle having said particular gauge.

16. The method of claim 15 further comprising:

while said needle is releasably attached to said needle guide, sliding the proximal end of said needle toward said proximal end of said probe, said needle following said angle of attack to a point under the skin of a patient to said focal point.

17. The method of claim 16 further comprising:

when said needle has been positioned under the skin of said patient, releasing said needle from said needle guide so that said probe can be removed while said needle remains positioned under said skin.

18. The method of claim 15 wherein said selecting comprises:

removing said needle guide from a plurality of needle guides of like gauge but having different angles of attacks, said plurality of needle guides being held by a common bond.

\* \* \* \* \*

UNITED STATES PATENT AND TRADEMARK OFFICE
CERTIFICATE OF CORRECTION

PATENT NO.       : 7,588,541 B2                                    Page 1 of 1
APPLICATION NO. : 10/766707
DATED            : September 15, 2009
INVENTOR(S)      : Floyd et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1544 days.

Signed and Sealed this

Twenty-first Day of September, 2010

David J. Kappos
*Director of the United States Patent and Trademark Office*